US006296358B1

(12) United States Patent
Cornsweet et al.

(10) Patent No.: US 6,296,358 B1
(45) Date of Patent: Oct. 2, 2001

(54) OCULAR FUNDUS AUTO IMAGER

(75) Inventors: Tom N. Cornsweet; Gary F. Buck, both of Prescott, AZ (US)

(73) Assignee: Visual Pathways, Inc., Prescott, AR (US)

( * ) Notice: Subject to any disclaimer, the term of this patent is extended or adjusted under 35 U.S.C. 154(b) by 0 days.

(21) Appl. No.: 09/649,462

(22) Filed: Aug. 25, 2000

Related U.S. Application Data (60) Provisional application No. 60/218,757, filed on Jul. 14, 2000.

(51) Int. Cl.[7] .................................................. A61B 3/14
(52) U.S. Cl. .................................................... 351/206
(58) Field of Search ......................... 351/200, 205, 351/206, 208, 209, 210, 213, 214, 216, 218, 221

(56) References Cited

U.S. PATENT DOCUMENTS

| | | | |
|---|---|---|---|
| 3,915,564 | 10/1975 | Urban | 351/7 |
| 4,187,014 | 2/1980 | Kato et al. | 354/62 |
| 4,283,124 | 8/1981 | Matsumura | 351/7 |
| 4,405,215 | 9/1983 | Sano et al. | 351/208 |
| 4,436,388 | 3/1984 | Takahashi et al. | 351/206 |
| 4,469,416 | 9/1984 | Isono | 351/206 |
| 4,579,430 | 4/1986 | Bille | 351/206 |
| 4,715,703 | 12/1987 | Cornsweet et al. | 351/205 |
| 5,090,799 | 2/1992 | Makino et al. | 351/221 |
| 5,129,400 | 7/1992 | Makino et al. | 128/666 |
| 5,233,517 | 8/1993 | Jindra | 364/413.13 |
| 5,371,557 | 12/1994 | Nanjho et al. | 351/206 |
| 5,382,988 | 1/1995 | Nanjo | 351/206 |
| 5,508,760 | 4/1996 | Kobayashi et al. | 351/221 |
| 5,572,266 | 11/1996 | Ohtsuka | 396/18 |
| 5,764,341 | 6/1998 | Fujieda et al. | 351/221 |
| 5,844,658 | 12/1998 | Kishida et al. | 351/206 |
| 5,912,720 | 6/1999 | Berger et al. | 351/206 |
| 5,914,771 | 6/1999 | Biber | 351/221 |
| 6,086,205 | * 7/2000 | Svetliza | 351/221 |

OTHER PUBLICATIONS

Abstract of U.S. Patent No. 4,019,813, Cornsweet, et al., issued Apr. 26, 1977, filed Jan. 19, 1976.
Abstract of U.S. Patent No. 4,281,926, Cornsweet, issued Aug. 4, 1981, filed Jul. 3, 1978.
Abstract of U.S. Patent No. 4,329,049, Rigg, et al., issued May 11, 1982, filed Mar. 6, 1880.
Abstract of U.S. Patent No. 4,715,703, Cornsweet, et al., issued Dec. 29, 1987, filed Jan. 14, 1986.
Abstract of U.S. Patent No. 5,114,222, Cornsweet, issued May 19, 1992, filed Dec. 11, 1989.
Abstract of U.S. Patent No. 5,210,554, Cornsweet, et al., issued May 11, 1993, filed Oct. 23, 1990.
Abstract of U.S. Patent No. 5,196,872, Beesmer, et al., issued Mar. 23, 1993, filed Oct. 23, 1990.
Abstract of U.S. Patent No. 5,410,376, Cornsweet, et al., issued Apr. 25, 1995, filed Feb. 4, 1994.
Abstract of U.S. Patent No. 5,422,690, Rothberg, et al., issued Jun. 6, 1995, filed Mar. 16, 1994.

* cited by examiner

*Primary Examiner*—George Manuel
(74) *Attorney, Agent, or Firm*—Cahill, Sutton & Thomas P.L.C.

(57) ABSTRACT

An ocular fundus imager automatically aligns fundus illuminating rays to enter the pupil and to prevent corneal reflections from obscuring the fundus image produced. Focusing the produced fundus image is automatically performed and is based upon the fundus image itself. A head restraint for the patient undergoing examination is in the form of a pair of spectacles which is not only easy to use accurately but significantly reduces the gross alignment between the optical system and the patient's pupil.

41 Claims, 8 Drawing Sheets

OCULAR FUNDUS AUTO IMAGER

CROSS REFERENCE TO RELATED APPLICATIONS

The present application claims priority to the subject matter disclosed in a provisional application entitled "FUNDUS AUTO IMAGER", filed Jul. 14, 2000 and assigned Ser. No. 60/218,757 directed to an invention made by the present inventor.

BACKGROUND OF THE INVENTION

1. Field of the Invention

The present invention relates to the field of ocular imaging, and, more particularly, to devices for imaging the ocular fundus.

2. Description of Related Art

The term ocular fundus refers to the inside back surface of the eye containing the retina, blood vessels, nerve fibers, and other structures. The appearance of the fundus is affected by a wide variety of pathologies, both ocular and systemic, such as glaucoma, macular degeneration, diabetes, and many others. For these reasons, most routine physical examinations and virtually all ophthalmic examinations include careful examination of the ocular fundus.

Routine examination of the ocular fundus (hereinafter referred to as fundus) is performed using an ophthalmoscope, which is a small, hand-held device that shines light through the patient's pupil to illuminate the fundus. The light reflected from the patient's fundus enters the examiner's eye, properly focused, so that the examiner can see the fundus structures.

If a hard copy of the fundus view is desired, a device called a fundus camera can be used. However, to use existing fundus cameras successfully is a very difficult undertaking. The operator must (1) position the fundus camera at the correct distance from the eye, (2) position it precisely in the vertical and horizontal directions in such a way that the light properly enters the pupil of the patient's eye, (3) refine the horizontal and vertical adjustments so that the light reflected from the front surface of the eye, the cornea, does not enter the camera, (4) position a visual target for the patient to look at so that the desired region of the fundus will be imaged, and (5) focus the fundus image. Al these operations must be performed on an eye that is often moving. Therefore, the use of existing fundus cameras requires a significant amount of training and skill; even the most skilled operators often collect a large number of images of a single eye in order to select one that is of good quality.

In existing fundus cameras, alignment and focusing are performed under visual control by the operator. This usually requires that the patient's eye be brightly illuminated. Such illumination would normally cause the pupils to constrict to a size too small to obtain good images. Therefore, most existing fundus cameras require that the patient's pupil be dilated by drugs.

U.S. Pat. No. 4,715,703 describes an invention made by one of the present inventors and discloses apparatus for analyzing the ocular fundus. The disclosure in this patent is incorporated herein by reference.

SUMMARY OF THE INVENTION

The present invention is in the nature of a fundus camera which automatically and quickly performs all the aligning and focusing functions. As a result, any unskilled person can learn to obtain high quality images after only a few minutes of training and the entire imaging procedure requires far less time than existing fundus cameras. Moreover, all of the automatic aligning and focusing procedures are performed using barely visible infrared illumination. With such illumination, the patient's pupils do not constrict and for all but patients with unusually small natural pupils, no artificial dilation is required. The fundus images can be obtained under infrared illumination and are acceptable for many purposes so that the patient need not be subjected to the extremely bright flashes required for existing fundus cameras. To obtain standard color images using the present invention, it is sometimes necessary to illuminate the eye with flashes of visible light. However, such images can be obtained in a time appreciably shorter than the reaction time of the pupil, so that the pupil constriction that results from the visible flash does not interfere with image collection. Unlike existing fundus cameras, the present invention provides for automatic selection of arbitrary wavelengths of the illuminating light. This facility has two significant advantages. First, it is possible to select illuminating wavelengths that enhance the visibility of certain fundus features. For example, certain near-infrared wavelengths render the early stages of macular degeneration more visible than under white illumination. Second, by careful selection of two or more wavelengths in the near infrared, it is possible to obtain a set of images which, when properly processed, generate a full color fundus image that appears very similar to a color image obtained with white light. Thus, it is possible to obtain acceptable color fundus images without subjecting the patient to bright flashes.

It is therefore a primary object of the present invention to provide a fundus imager which automatically positions fundus illuminating radiation to enter the pupil while preventing reflection from the cornea from obscuring the fundus image, irrespective of movement of the eye or the patient's head within the head restraint.

Another object of the present invention is to provide automatic focusing of the fundus image based upon the image itself.

Yet another object of the present invention is to provide automatic positioning of one or a sequence of fixation targets to select the sections(s) of the fundus to be imaged.

Still another object of the present invention is to provide a fundus imager for collecting a set of images that can be arranged in a montage to provide a very wide angle fundus image facilitated by the capability of the fundus imager to automatically align and focus the images.

A further object of the present invention is to provide automatic setting of video levels in a fundus imager to use the full range of levels available.

Yet another object of the present invention is to permit aligning and focusing a fundus imager under infrared illumination to permit imaging without drug induced dilation of the pupil.

A yet further object of the present invention is to provide for automatic selection of illumination wavelength.

A yet further object of the present invention is to provide a colored image from a fundus imager by sequential imaging and registration of images.

A yet further object of the present invention is to provide an apparently normally colored image generated by two infrared wavelengths.

A yet further object of the present invention is to provide for automatic acquisition by a fundus imager of a stereo image pair having a known stereo base.

A yet further object of the present invention is to provide a head positioning spectacle frame for use with a fundus imager.

A yet further object of the present invention is to accommodate for astigmatism and/or extreme near and far sightedness by placing a lens of the patient's glasses in the path of illumination of the fundus imager.

A yet further object of the present invention is to provide a method for automatically positioning the illuminating radiation of a fundus imager to prevent corneal reflections from obscuring the fundus image obtained.

A yet further object of the present invention is to provide a method for automatic focusing in a fundus imager.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which.

DESCRIPTION OF THE PREFERRED EMBODIMENT

Figure 1:
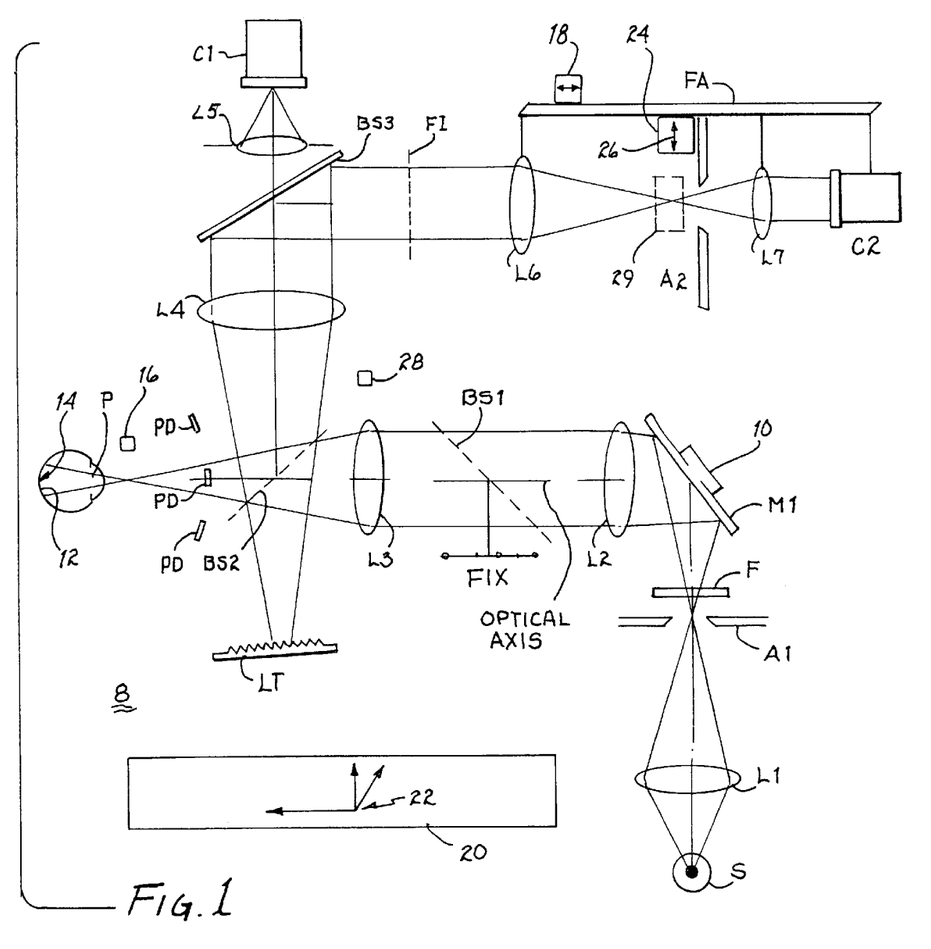
FIG. 1 is a schematic diagram illustrating the functional elements of the present invention.

Referring to FIG. 1, there is illustrated a preferred embodiment of optical system 8 of the present invention. Lens L1 focuses light from a light source S onto a small aperture A1. The light source may be a source of visible light, infrared radiation or of a wavelength in the near visible infrared region. Light passing through aperture A1 passes through a filter F and is reflected by mirror M1 toward lens L2. Mirror M1 is pivotally mounted to permit rotation about two orthogonal axes, which pivotal mounting is represented by device 10 attached to the mirror. Lens L2 collimates (makes parallel) light from aperture A1. A beam splitter BS1 transmits about ninety percent (90%) of the incident light from lens L2 to lens L3. Half of the light passing through lens L3 is reflected by beam splitter BS2 and is absorbed by light trap LT. The other half of the light passing through lens L3 forms an image of aperture A1 in the focal plane of lens L3, which focal plane lies in the plane of a patient's pupil P. The light passing through the pupil illuminates a section 12 of ocular fundus 14 (hereinafter only the term fundus will be used).

Light diffusely reflected from fundus 14 emerges from pupil P and half of it is reflected by beam splitter BS2 toward collimating lens L4, which lens is at its focal distance from the pupil. An infrared light emitting diode (LED), representatively shown and identified by reference numeral 16, diffusely illuminates the region of the front of the eye. About ten percent (10%) of the light is transmitted through beam splitter BS3, which light passes through lens L5. Lens L5 forms an image of the pupil and the front of the eye in the plane of a video sensor C1. The video output from video sensor C1 is displayed on an operator's monitor (on computer screen shown in FIG. 3) to provide a view of the eye and of the pupil.

If the patient's eye is focused at infinity, the light reflected from each point on fundus 14 will be collimated as it is incident on lens L4. Therefore, 90% of the light reflected from beam splitter BS3 will form an aerial image of the fundus in the focal plane of lens L4, which focal plane is represented by a dashed line identified as FI (Fundus Image). The light passes through lens L6, which lens is at its focal distance from fundus image FI. Thus, lens L6 will collimate light from each point on the fundus. Further, because the light considered as originating in the plane of pupil P is collimated by lens L4, lens L6 will form an image of the pupil in its back focal plane, which is coincident with the location of second aperture A2. Light passing through second aperture A2 is incident on lens L7, which lens will then form an image of the fundus in its back focal plane which is coincident with second video sensor C2. The video image produced by video sensor C2 represents an image of the fundus.

If the eye is not focused at infinity, the aerial fundus image FI will be moved away from the back focal plane of lens L4. For example, if the eye is nearsighted, the aerial fundus image will move toward lens L4. Such movement would cause the fundus image to be defocused on video sensor C2. Focusing the image under these conditions is accomplished as follows. Lens L6, aperture A2, lens L7, and video sensor C2 are mechanically connected to one another by a focusing assembly labeled FA; that is, these elements are fixedly positioned relative to one another and move as a unit upon movement of the focusing assembly. A unit identified by reference numeral 18 provides rectilinear movement of the focusing assembly on demand.

Figure 2:
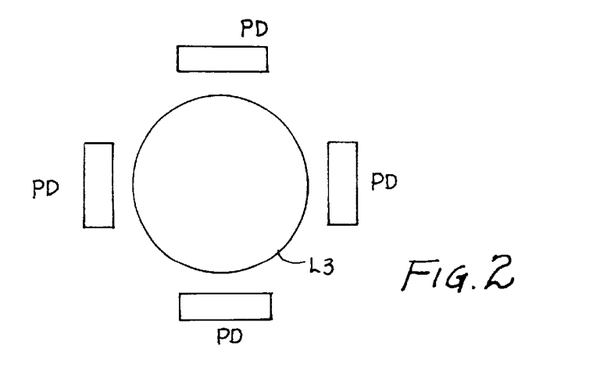
FIG. 2 illustrates the location of the photo detectors relative to lens L3.

A set of photodetectors PD, of which three are shown in FIG. 1, lie in a plane between the eye and beam splitter BS2. As further shown in FIG. 2 from the viewpoint of the eye, orthogonal pairs of photodetectors are located in the vertical and horizontal axes relative to lens L3. The purpose of these photodetectors is that of sensing any light diffusely reflected from the iris.

The entire optical system (8) discussed above and illustrated in FIG. 1 is supported upon an assembly identified by reference numeral 20. The assembly includes motive elements, such as rectilinear actuators and related servo-mechanisms responsive to commands for translating the entire optical system horizontally (laterally), vertically and toward and away from the eye, as representatively depicted by set of arrows 22.

Figure 3:
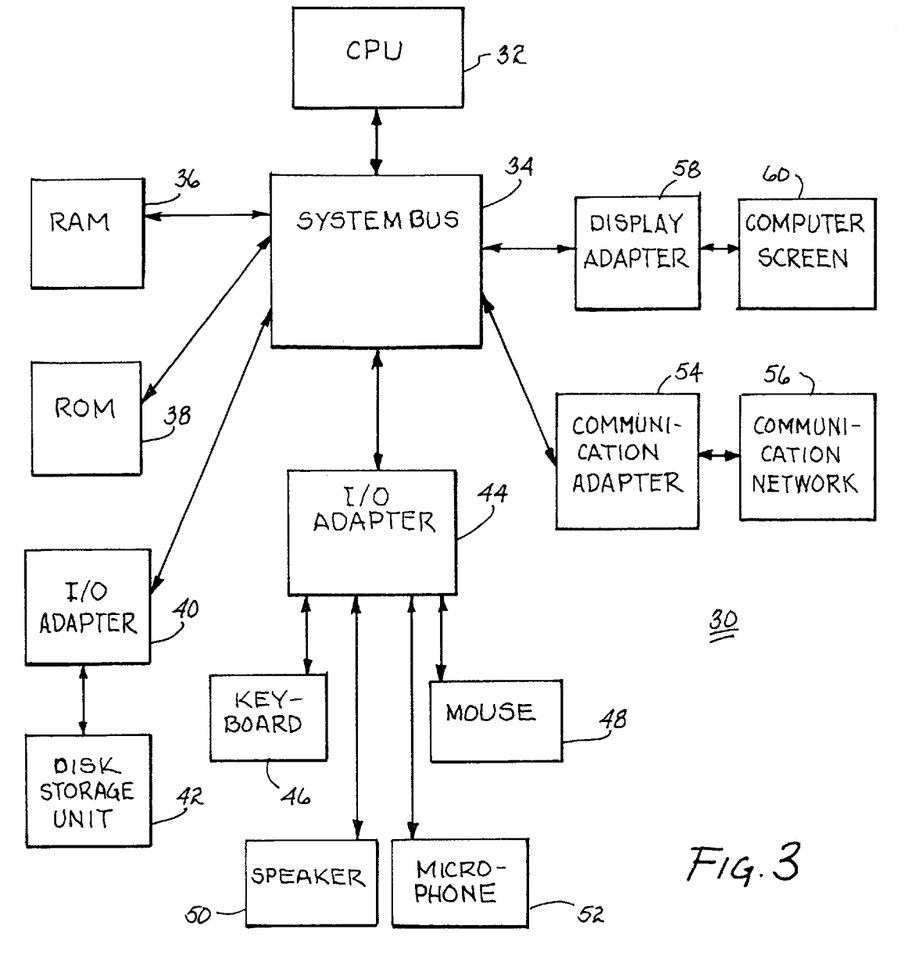
FIG. 3 is a block diagram illustrating a representative computer system for operating the present invention.

To operate optical system 8, a computer control system 30 is required, which is representatively illustrated in FIG. 3. The computer control system includes a central processing unit (CPU) 32, such as a microprocessor, and a number of units interconnected via a system bus 34. A random access memory (RAM) 36, a read only memory (ROM) 38 are incorporated. An input/output adapter 40 interconnects peripheral devices, such as a disk storage unit 42. A user interface adapter 44 connects the keyboard 46, a mouse (or trackball) 48, a speaker 50, a microphone 52, and/or other user interface devices, such as a touch screen (not shown) with system bus 34. A communication adapter 54 interconnects the above described optical system 8 through a communication network 56. A display adapter 58 interconnects a display unit 60, which maybe a video screen, monitor, or the like. The computer operating system employed maybe any one of presently commercially available operating systems.

In operation, an operator enters patient information data into the computer control system using the keyboard and also enters the location or set of locations on the fundus that is/are to be imaged. It may be noted that the field of view of the optical system is preferably 30° in diameter while the ocular fundus is about 200° in diameter. To image various regions of the 200° fundus, the eye can be rotated with respect to the optical system; such rotation is achieved by having the patient look from one reference point to another. After entry of the raw data, the patient's head is juxtaposed with a head positioning apparatus to locate the eye in approximate alignment with respect to the optical axis. An image of the front of the eye produced by video sensor C1 appears on computer screen 60. The operator may use a trackball or mouse 48 or similar control to move the image horizontally and vertically until the pupil is approximately centered on a set of cross-hairs displayed on the computer screen. A further control is used to focus the image of a pupil. Such horizontal and vertical movements, along with focusing of the image of the pupil, are achieved by moving the entire optical system 8 through energization of assembly 20 (see FIG. 1). That is, the horizontal and vertical movements of the image are achieved by moving the entire optical system horizontally and vertically and the focusing of the pupil image is accomplished by moving the entire optical system toward or away from the eye. When the operator is satisfied that the pupil image is in sharp focus and that the pupil is approximately centered, the operator deenergizes LED 16 (which illuminated the front of the eye) and then initiates the automatic alignment and image collection procedure.

To achieve proper alignment of the optical system with the eye requires that the light from light source S enter the pupil. Initially, the angular position of mirror M1 is set so that the image of aperture A1 lies on the optical axis of the system. It is noted that the image of aperture A1 contains the light used to illuminate the fundus. Since video sensor C1 also lies on the optical axis, if the operator has initially centered the pupil image even crudely, light from light source S will enter the pupil. About three percent (3%) of the light incident on the eye will be reflected from the corneal surface and if this light reaches video sensor C2, it would seriously obscure the image of the fundus. Therefore, the optical system includes the following elements for preventing corneal reflection from reaching video sensor C2.

Figure 4:
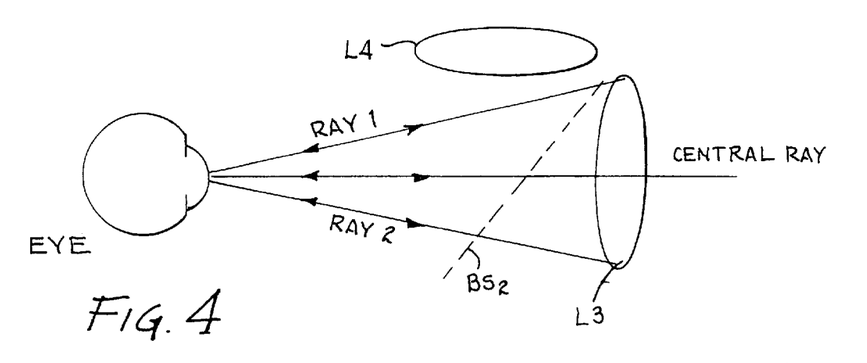
FIG. 4 illustrates the effect of corneal reflections to be avoided.

If the light rays forming the image of aperture A1 were aligned so that the central ray were perpendicular to the corneal surface, then many of the rays in the corneal reflection would pass backward along the incident light paths. As shown in FIG. 4, the central ray would pass back on itself; the ray labeled Ray-1 would pass back along the path of the incident ray labeled Ray-2, etc. (The angle at which a ray is reflected from a shiny surface can be determined as follows. First, find the line that is perpendicular to the surface at the point that the ray hits. Then find the angle between the incident ray and the perpendicular ray; this is called the "angle of incidence". Finally, the ray will be reflected at an angle equal to the angle of incidence but on the other side of the perpendicular line. This is called the angle of reflection.) It is therefore evident from the schematic shown in FIG. 4 that many rays reflected from the corneal surface and impinging upon beam splitter BS2 would enter lens L4 and impinge upon video sensor C2.

Figure 5:
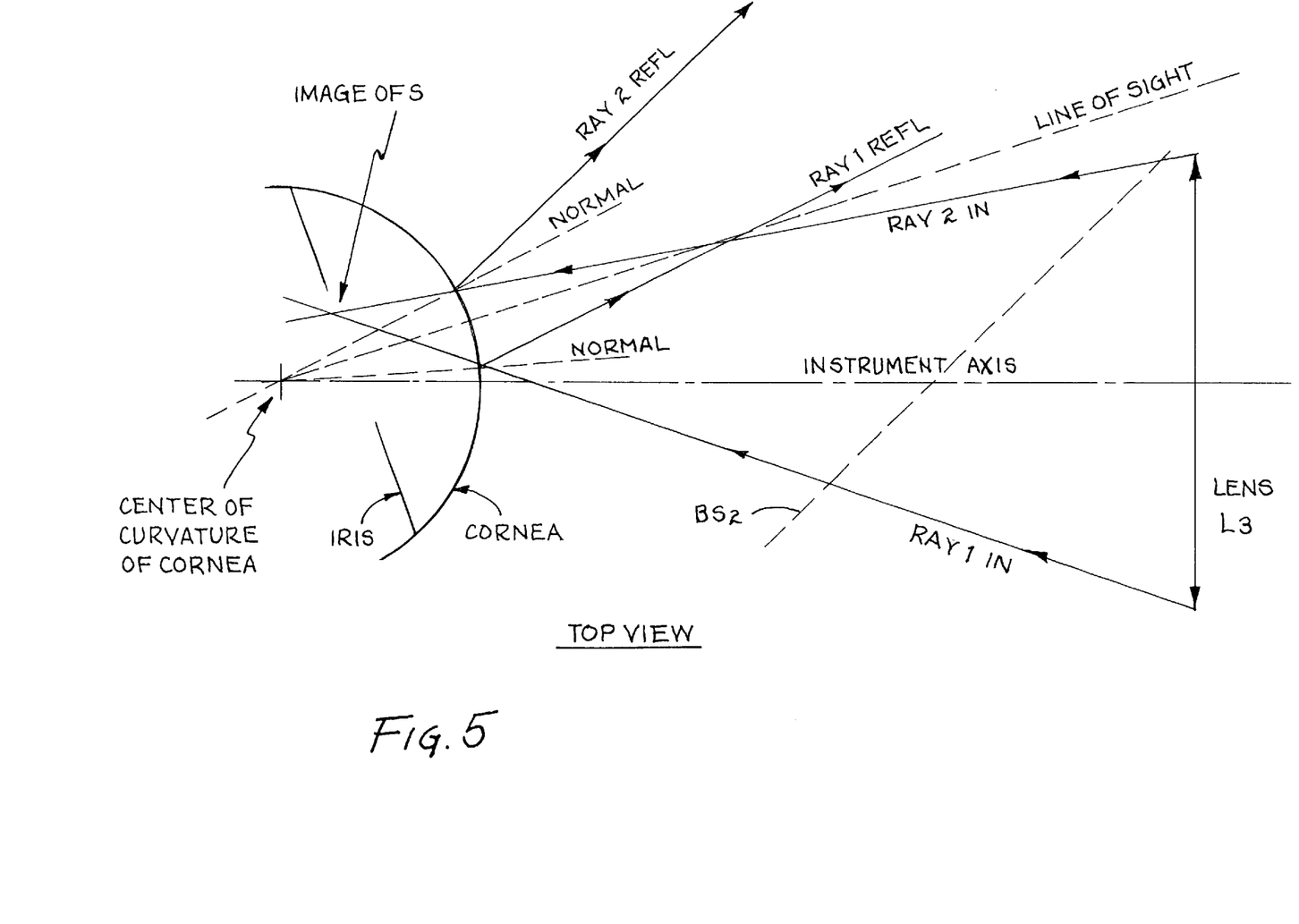
FIG. 5 is a schematic illustrating an alignment of the optical axis to avoid corneal reflections.

However, the corneal surface is steeply curved and if the central ray of the incident light is moved far enough away from the perpendicular to the cornea, as shown in FIG. 5, the reflected light will be deflected far enough to miss beam splitter BS2 and therefore miss passing through lens L4 and therefore not impinge upon video sensor C2. The method for achieving this deflection will be described below.

The image of aperture A1 is appreciably smaller than the smallest pupil for which optical system 8 will operate correctly. In the preferred environment, the smallest useful pupil is four millimeters (4 mm) in diameter and the image aperture A1 is one millimeter (1 mm) in diameter. Initially, the image of aperture of A1 lies on the optical axis and is thus approximately centered on the pupil. Mirror M1 is actuated by signals generated by the computer system to rotate about a vertical axis to cause the image of aperture A1, and thus the light that illuminates the fundus, to move horizontally, laterally in small increments (e.g. 0.1 millimeters), to the left across the pupil. When the image of aperture A1 just begins to fall beyond the pupil, that is to fall upon the iris, the light scattered by the iris will fall on all four photo detectors PD (see FIG. 2). The photodetectors become enabled to generate a signal supplied to the computer system indicative of such event. Thereafter, the image of aperture of A1 is moved backward one step and a video image of the fundus is saved. Mirror M1 is then moved back to the center and stepped in increments toward the top of the pupil until the photo detectors indicate light reflected from the iris. Thereafter, the image of aperture A1 is moved backward one step and a video image of the fundus is saved. This step is repeated for each of the right and bottom edges of the pupil.

The computer now contains four fundus images taken with light at four locations at the edge of the pupil. If the corneal reflection has reached video sensor C2 in one of those images, the amount of light forming that image will be greater then the light forming the other images. The computer system examines each of the four images and selects the one for which the average video level is lowest. This image is presumed not to contain light from any corneal reflection. It may be noted that the geometry of the cornea and pupil are such that for a pupil four millimeters (4 mm) or larger, the corneal (but not iris) reflection will always be absent from at least one of the four images.

When the image of aperture A1 falls on the iris, the diffuse reflection will illuminate all four detectors. Most of the time that the image of aperture A1 falls on the pupil and not the iris, the corneal reflection will illuminate one or two photo detectors. However, the corneal reflection will never fall on all four detectors. Therefore, to achieve the goal of placing the image of aperture A1 into the pupil, it is necessary to determine location of the edge of the pupil by moving the image of aperture A1 until all four of the four detectors simultaneously generate a signal indictive that they are illuminated.

The four edges of the pupil are located as a function of the signals generated by the photodetectors, as described above. From the location of these edges, the center of the pupil can be determined by the computer system with respect to the optical axis of the instrument. If the center of the pupil does not lie approximately on the optical axis, the computer system commands the horizontal and vertical motors (assembly 20) to move the entire optical system 8 until the pupil is centered. The servomechanisms actuating the horizontal and vertical motors are slow compared to the motions of mirror M1. These servomechanisms are intended to permit limiting the motions of mirror M1 within a restricted range to reduce the sizes of the entrance and exit pupils of the optical system and to simplify the optical design of the lenses. In this way, light is continuously and automatically introduced through the pupil to illuminate the fundus and images contaminated by light reflected from the cornea surface can be automatically discarded.

An alternative method for tracking the pupil and positioning the image of aperture A1 on the pupil of the eye will be described hereafter. In the above described procedure, an image of the patient's pupil is formed on video sensor C1. The image was used by the operator to perform rough alignment of the optical system with the eye. However, image appearing on video sensor C1 can also be used for automatic tracking of the eye and the positioning of the image of aperture A1. This is done by using the computer system for extracting the edges of the pupil from the video signal and computing the coordinates of its center and of its edges.

When the image of aperture A1 falls within the pupil, the light it contains passes through the pupil, falls on the fundus and is scattered by the fundus. Some of that scattered light exits the pupil. Thus, when the image of aperture A1 falls within the pupil, the pupil is backlighted by light reflected from the fundus, and an image of the pupil on video sensor C1 consists of a bright disk on a dark background. The goal is to determine the location of the center and of the edges of this image so that aperture A1 can be automatically placed where the fundus will be illuminated and the image of the fundus on video sensor C2 will then not be spoiled by light reflected from the cornea. If the pupil is correctly centered on the optical axis of the optical system, the pupil image will be centered. If not, the direction and distance between the center of the pupil and the center of the field of view of the camera can be used to drive servomechanisms (assembly 20 in FIG. 1) to correct the error by moving the entire optical system. Further, if the edges of the pupil are located, those locations can be used to position the image of aperture A1 just inside the edge of the pupil. There are a number of ways of finding the center and the edges of the pupil image from the video signal produced.

Figure 6:
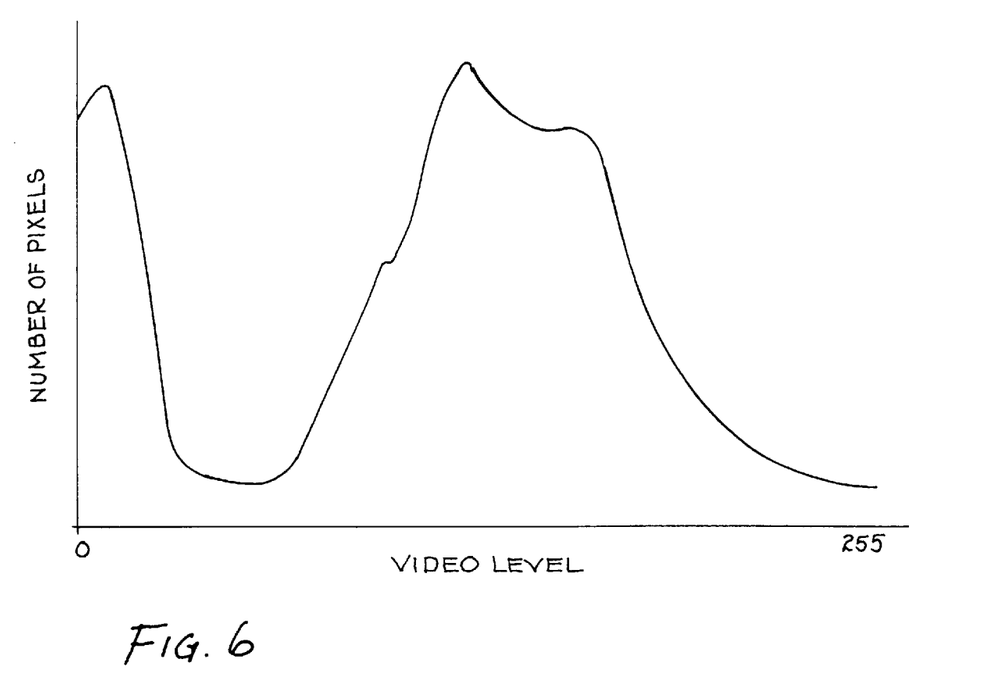
FIG. 6 is a graph illustrating determination of an acceptable video level.

A method for finding the center and the edges of the pupil image will now be described. It involves finding the edges of the pupil image on each video line that intersects the edges and then computing the most likely position of the center and of the edges of the actual pupil. The image from video sensor C1 is read out, as is the standard video practice, by reading the values of the various points along a horizontal line and then the values along the next horizontal line, etc. (neglecting the detail of interlacing). If a given video horizontal line intercepts the image of the pupil, the video level will abruptly rise from the dark background level to the brighter level of the pupil. To locate this transition and find the position of each edge, it is necessary to define the values of the background and of the pupil. To do this, a histogram of pixei values is formed during the first few video frames. It will contain a large peak with values near zero, representing dark background pixels, and additional peaks at higher values that represent the pupil and various reflections to be discussed below. A typical histogram is illustrated in FIG. 6. Each point along the horizontal axis represents a different video signal level and each point on the vertical axis indicates the area of the image that displays the corresponding video level.

The "background level" is defined as the level just below the first minimum. Specifically, the histogram is first smoothed using a running block filter. That is, for a position on the horizontal axis the vertical value on the curve is replaced by the average of the vertical value and its adjoining values. This computation is performed in steps along the horizontal axis (video level) until there are ten consecutive values for which the vertical axis increases. The "background value" is then defined as the lowest of these ten values. An "edge point" on each horizontal line is defined as the horizontal location for which the video level changes from equal to or below the "background value" to above that value or changes from above that value to equal or below that value. As the video scan proceeds, the location of each point is saved. Thus, at the end of each video frame, a set of point locations is stored in the computer memory (see FIG. 3).

Figure 7:
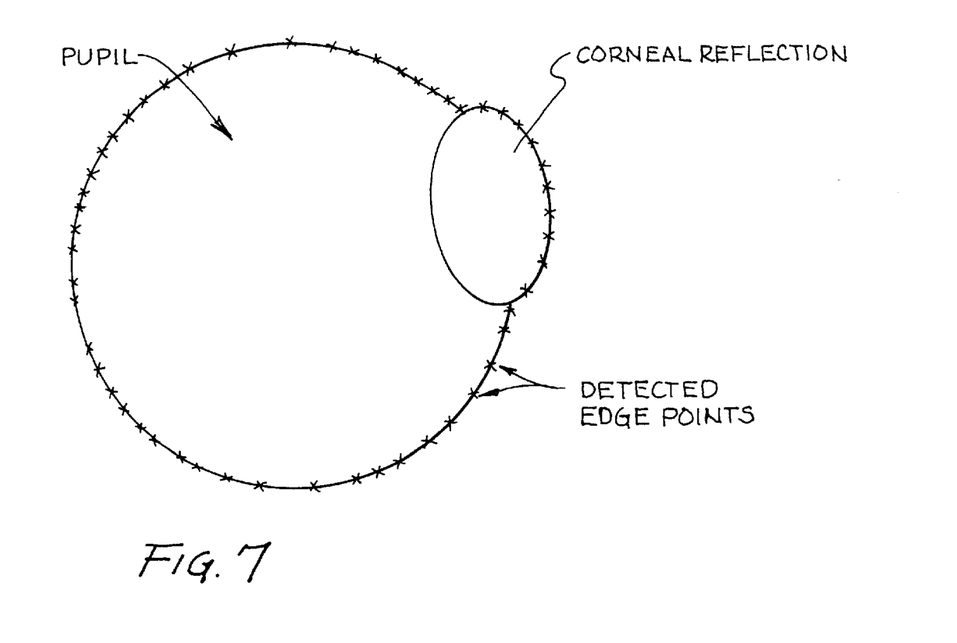
FIG. 7 illustrates determination of edge points.

If the pupil image consists solely of a bright disk on a dark background, the above described procedure would essentially always be successful in finding a close approximation to the actual pupil edges. However, for real pupil images the procedure is confounded by two sources of reflections. First, light reflected from the cornea; if this light reaches video sensor C1, it will form a bright spot superimposed on the pupil image. If that spot were entirely within the margins of the pupil, it would not interfere with the process described above. However, if it falls on the edge of the pupil image, as it may when a patient is looking at an angle to the optical axis of the optical system, then it will appear as a bulge on the edge of the pupil, as illustrated in FIG. 7. Therefore, some of the "edge points" located by the above computations will actually be edges of the corneal reflection instead of the edge of the pupil. Second, a similar problem arises if the image of aperture A1 falls on the edge of the pupil, as it might during an eye movement too fast to be accurately tracked and compensated. In that event, finding the center and the edges of the pupil requires special procedures.

One such special procedure will described below. The edge points are collected as described above. There will typically be several hundred such points. An ellipse is then found (determined) that best fits the set of edge points. The pupil of the human eye is usually circular, but if it is viewed from an angle, as it will be if the patient is looking at a point other than on the optical axis, then the image of the pupil will approximate an ellipse. So long as the reflections from the cornea and iris do not overlap a major part of the pupil edge (and so long as the pupil is not of grossly abnormal shape), such a procedure yields a good estimate of the locations of the actual pupil center and the edge.

One method for finding the best fitting ellipse will be described. Assuming that 200 hundred points have been labeled edge points by the above procedure, each of such points has a horizontal (x) and a vertical (y) location. Assume that these 200 hundred points, that is pairs of values (x,y), are in a consecutive list. Five points are selected at random from the list, requiring only that each selected point be separated from the next selected point by ten or so positions on the list. This process will then yield the locations of five putative edge points that are some distances apart on the pupil. These five pairs of values are substituted into the equation for an ellipse and solved for the five ellipse parameters. One form of equation for an ellipse is:

$$c1*x^2 + c2*xy + c3*y^2 + c4*x + c5*y = 1$$

Substitute the five putative edge points as the pairs (x,y) of values in that equation. Invert the matrix to find the values for c1 through c5. Then the angle that the ellipse makes with the xy axis is:

$$\theta = \frac{1}{2} * \text{arc cot}((c1-c3)/c2)$$

Then if $u = x*\cos\theta + y*\sin\theta$ and $v = -x*\sin\theta + y*\cos\theta$, then $$d1*u^2 + d3*v^2 + d4*u + d5*v = 1$$

Where $$d1 = c1*\cos^2\theta + c2*\cos\theta*\sin\theta + c3*\sin^2\theta$$

$$d3 = c1*\sin^2\theta - c2*\cos\theta*\sin\theta + c3*\cos^2\theta$$

$$d4 = c4*\cos\theta + c5*\sin\theta$$

$$d5 = -c4*\sin\theta + c5*\cos\theta$$

The center of the ellipse has u coordinate $u = -d4/(s*d1)$ and v coordinate $V = -d5/(2*d3)$ so the center of the ellipse has the x coordinate $$x = u*\cos\theta - v*\sin\theta$$

and the y coordinate $$y = u*\sin\theta + v*\cos\theta$$

If $R = 1 + d4^2/2d1 + d5^2/2d3$ then the semiaxes of the ellipse have lengths Square root (R/d1) and square root ( R/d3) This entire procedure is repeated, say, 100 times for 100 different sets of putative points yielding 100 different estimates of the x,y location of the center. The best fitting ellipse is the one for which the center is closest to the median x and y values of the set of 100.

The resulting deviations between the horizontal and the vertical locations of the center of the chosen ellipse and the optical axis of the optical system can be used directly as error signals to drive the positioning servos associated with assembly 20 and the image of aperture A1 can be directly and finely positioned such as by moving mirror M1 so that the image lies just inside the pupil.

The corneal reflections can be prevented from spoiling the image of the fundus by the following procedure. The method involves directing the patient's line of sight to certain selected positions. If the selected position is straight ahead, that is, the line of sight is directed along the optical axis, then positioning the image of aperture A1 in any direction at the margin of the pupil will cause the corneal reflection to be sufficiently deflected (assuming a pupil of 4 mm diameter or larger). If the selected position is in any other direction, then positioning the image of aperture A1 on the same side of the pupil will cause the reflections to be sufficiently deflected (see FIG. 5). For example if the patient is looking to the left and the image of aperture of A1 is positioned at the left margin of the pupil, the corneal reflection will be deflected far enough to miss lens L4.

An automatic focusing method will be described with reference to FIG. 1. Aperture A2 is a hole significantly smaller then the image of the pupil and which is conjugate with the pupil; that is, it is in the same plane as the image of the pupil. In the preferred embodiment, aperture A2 is a rectangular aperture one millimeter (1 mm ) wide and two millimeter (2 mm ) high. Aperture A2 is mounted on a linear actuator 24 that can move it rapidly in a horizontal direction, as depicted by arrows 26. In the alignment method described above, the image of aperture A1 is made to lie near the edge of the pupil and a fundus image is saved. To focus, two images are saved in rapid succession, one with aperture A2 lying to the right of the center of the pupil image and the second with aperture A2 lying to the left of the center of the pupil image, by enabling linear actuator 24. If the focusing assembly FA is positioned so that the fundus image FI lies in the focal plane of lens L6 (the fundus image is thus correctly focused on video sensor C2) then the two images taken with aperture A2 in each of its two positions will be in registry and superimposable. However, if focusing assembly FA is not correctly positioned and the image is out of focus, then one of the images will be horizontally displaced with respect to the other. With the particular optical arrangement illustrated in FIG. 1, the direction of the displacement indicates the direction that focusing assembly FA must move to achieve correct focus and the size of that displacement is directly proportional to the distance the focusing assembly must move to correct focus.

Figure 8A:
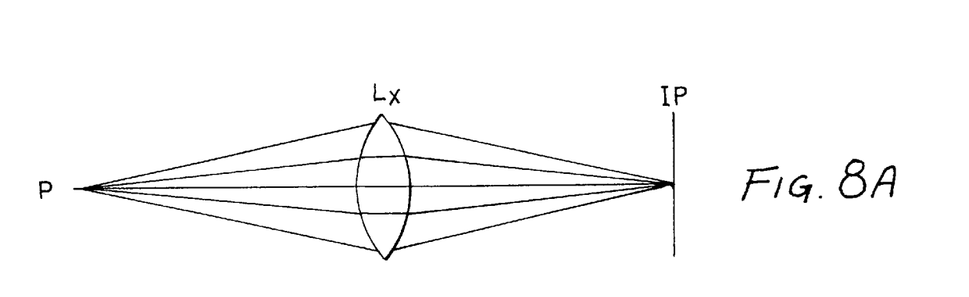
FIGS. 8A, 8B and 8C depict the light rays from a point to an image plane without an interposed aperture, and with an interposed aperture at two locations displaced from one another.
Figure 8B:
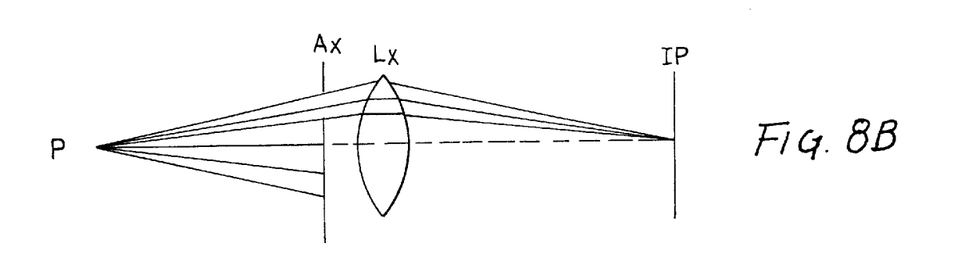
Figure 8C:
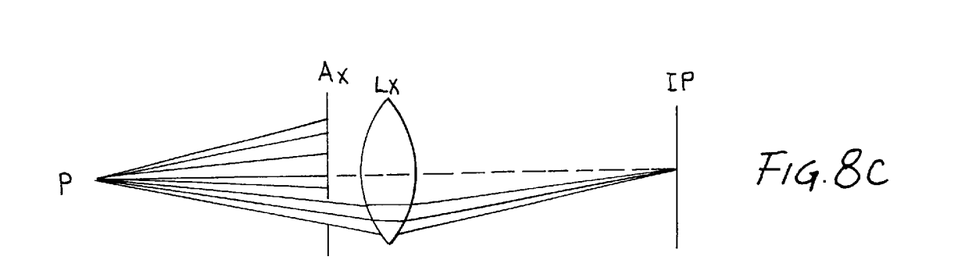
Figure 9A:
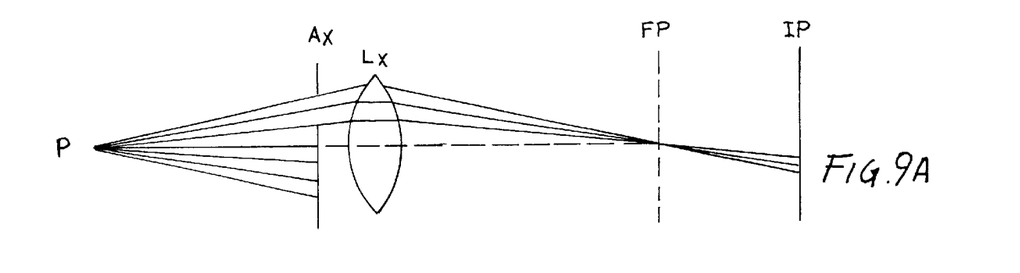
FIGS. 9A and 9B illustrate the shift of an image upon an image plane located beyond the focal plane in response to displacement of an interposed aperture from one location to another.
Figure 9B:
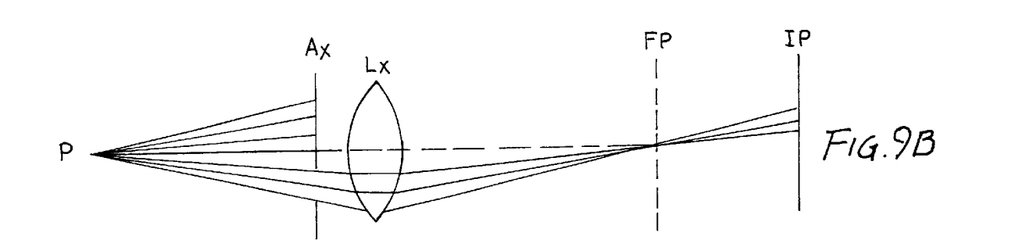
Figure 10A:
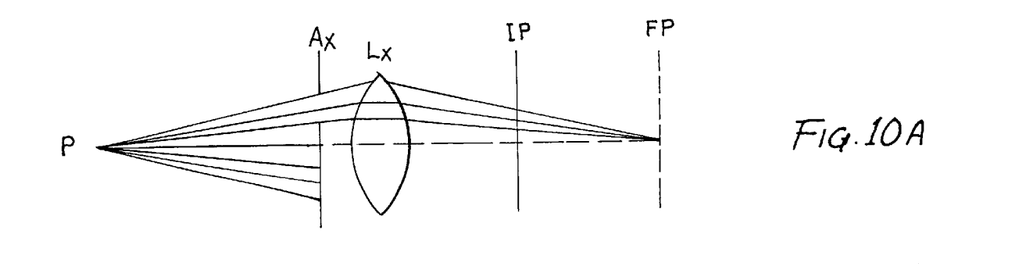
FIGS. 10A and 10B illustrate the shift of an image upon an image plane located short of the focal plane in response to displacement of an interposed aperture from one location to another.
Figure 10B:
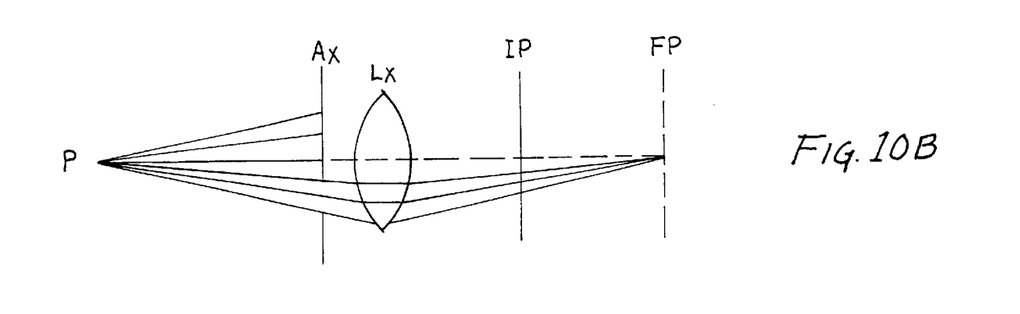

To explain more clearly the direction of displacement of the focusing assembly (FA) to achieve correct focus, joint reference will be made to FIGS. 8A, 8B, 8C, 9A, 9B, 10A and 10B. As shown in FIG. 8A, lens Lx forms an image of a point P that is sharply focused on image plane IP. If the aperture of an apertured plate Ax is placed between point P and lens Lx off the optical axis, the image of point P will be in focus on image plane IP, as shown in FIG. 8B. However, because certain of the rays are excluded by the plate, the intensity of the image on the image plane will be reduced. As depicted in FIG. 8C, displacement of the aperture in apertured plate Ax will have no effect upon the location of the image of point P on the image plane. If the image plane IP is displaced from the focal plane FP, as depicted in FIG. 9A, a blurred image of point P will appear on the image plane at a location diametrically opposed relative to the optical axis from the aperture in apertured plate Ax. When the apertured plate is displaced (like the displacement shown in FIG. 8C), the blurred image on the image plane will be displaced in a direction opposite from the displacement of the apertured plate, as shown in FIG. 9B. If image plane IP is short of the focal plane FP, as shown in FIG. 10A, the rays passing through the aperture of apertured plate Ax will form a blurred image of point P on the image plane. This blurred image will be on the same side of the optical axis as is the aperture. If the apertured plate is displaced (like the displacement shown in FIG. 8C), the blurred image of point P on the image plane will be displaced in the same direction, as shown in FIG. 10B. From this analysis, the following conclusions are evident. If the image is in focus on the image plane, any shift of an apertured plate will not affect the position of the image in the image plane. If the image plane is beyond the focal plane, the image on the image plane will shift in a direction opposite to the direction of displacement of the aperture. Congruously, if the focal plane is beyond the image plane, the image on the image plane will shift in the same direction as the aperture is displaced. From these relationships, it is a simple computational exercise performable by the computer system illustrated in FIG. 3 to determine the direction and amount of displacement of focal assembly FA necessary to place the image of the fundus in focus on video screen C2.

Thereby, automatic focusing is achieved by finding the displacement of one image of a pair of images that is required to bring the two images into registry and then moving the focusing assembly in accordance with such result. The required displacement can be found by computing a cross-correlation function between the two images. This is a mathematical computation that, in effect, lays one image on top of the other, measures how well the two images correspond, then shifts one image horizontally a little with respect to the other, measures the correspondence again, shifts the one image a little more and measures the correspondence again and repeats these steps for a large number of relative positions of two images. Finally, the shift that produces the best correspondence is computed.

Even when a patient is trying to hold his/her eye steady, the eye is always moving and as a result the fundus image is continually shifting across the sensing surface of video sensor C2. Exposure durations for individual images are chosen to be short enough (about 15 milliseconds) that this motion does not cause significant blur. Nevertheless, the time interval between members of pairs of images taken during the automatic focusing procedure may be long enough to allow movement between the images that would confound the focusing algorithm. Therefore, the actual procedure requires that a number of pairs of images be collected and the average displacement computed as the measure of focus error.

Selection of the fundus region to be imaged will now be described. Adjacent beam splitter BS1 illustrated in FIG. 1 lies a set of dots labeled FIX. Each dot represents a visible light emitting diode (LED). Beam splitter BS1 reflects about 10% of the light from these LED's toward lens L3 and the eye. The set of dots (FIX) lies in the back focal plane of lens L3 and these LED's appear to the eye as if they were a long distance away. Only one of the LED's is illuminated at any given time and the patient is asked to look at it. When the patient looks at the illuminated LED, the location of the LED with respect to the optical axis of the instrument determines the location on the fundus that will be illuminated and imaged. For example, if the LED that lies on the optical axis is turned on and the patient fixates it, then the image will be centered on the fovea or macula. If the illuminated LED is 17° to the patient's left, then the region of the fundus imaged has its center 17° to the left of the macula (as observed from the front of the eye).

In addition to the LED's in the plane labeled FIX, other visible LED's, such as LED 28 shown in FIG. 1, are positioned at various angular displacements from the optical axis, lying, such as to the sides of lens L3. When one of these LED's is turned on, it does not appear at optical infinity but nevertheless the patient can successfully fixate it to yield a view of more peripheral fundus features.

When the operator sets up the instrument prior to collecting images, he/she selects the region or set of regions of the fundus to be imaged. If just one region is to be imaged, the appropriate LED will be lighted. If a series of locations is to be imaged, the computer (see FIG. 3) automatically selects the LED corresponding to the first location; after the image has been collected, the remaining selected LED's are lighted in sequence until the desired sequence of images has been obtained. If such a sequence involves locations that are widely separated so that the patient must make a significant eye movement to refixate, then the computer commands the horizontal and vertical positioning servo mechanisms of assembly 20 to move the optical system 8 (and optical axis) to the position where the center of the pupil is expected to be after the fixation movement. This eases the task of the servo loop that acts on mirror M1 and its limited repositioning capability.

After the image of aperture A1 has been located to exclude the corneal reflection and focusing has been achieved, another pair of images is collected with aperture A2 in each of two positions. This pair of images constitutes a stereo pair of images with a known stereo base, which base is the distance through which aperture A2 has moved.

During the alignment and focusing procedures previously described, filter F (see FIG. 1) blocks visible light but transmits near infrared wavelength radiation. To obtain an image or set of images in infrared illumination, this filter need not be changed. For certain forms of colored images, it is necessary to collect an image, rapidly change the filter to one transmitting a different wavelength band, acquire another image and return the infrared filter. The result is two or more images, each taken in a different wavelength band. To display a single color image, the different images are used to drive different color guns in a display device. For example, if one image is collected in red illumination and a second is collected in green illumination then the red image is made to drive the red gun in the display device and the green image is made to drive the green gun in the display device. The combined images will appear as a normal (two color) image.

During the interval between images collected in different wavelengths, it is possible that the eye, and thus the fundus image, will move significantly. If such movement occurs, then the variously colored images would not be in registry when displayed. To prevent this occurrence the images are automatically registered before being displayed by performing a two-dimensional cross-correlation and then shifting the images in accordance with the result.

Figure 11:
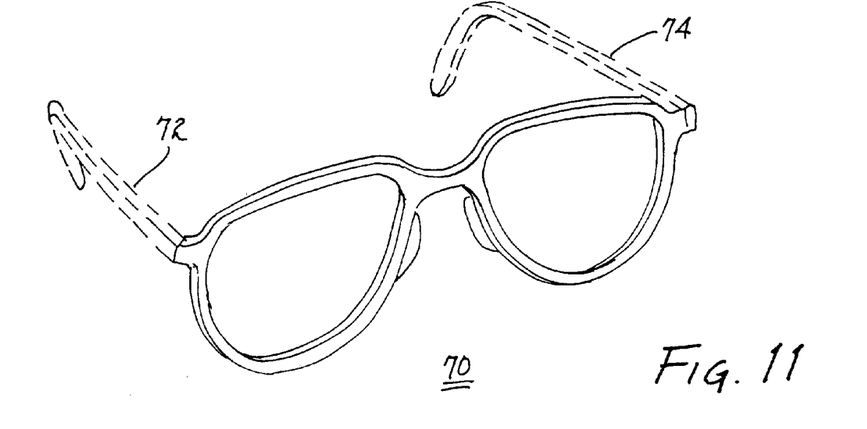
FIG. 11 illustrates a head restraint in the form of a pair of spectacles.

Essentially all standard ophthalmic instruments position a patient's head using a combination of a chin rest and a forehead rest. Typically, the chin rest is manually raised or lowered to bring the eye to about the right height. The present invention employs a different apparatus for positioning a patient's head and therefore eye. As shown in FIG. 11, a frame 70 of a standard pair of spectacles is mounted on the case or other support of the instrument (not shown); preferably, temple pieces 72, 74 are omitted and therefore shown in dashed lines. The patient is instructed to place his/her head in the frame of the spectacles. Because spectacles are so familiar, little instruction is actually needed. The variations in the location of the eyes with respect to the bridge of the nose is such that virtually all eyes will fall within a cube that is fixed with respect to the instrument and is about 20 millimeters on a side. This is a much smaller variation then is encountered by using the usual chin and forehead rest apparatus. Thus, the commonality and uniformity of the location of the eyes with respect to the spectacles requires a very small range of accommodating movement of optical system 8. Furthermore, properly chosen spectacle frames constrain head movement appreciably better than a chin and forehead rest apparatus; thus, the requirement for an automatic tracking system is reduced.

The motion of focusing assembly FA (see FIG. 1) compensates for a patient's spherical refractive error (near or farsightedness) but does not correct for astigmatism. Because the fundus images are collected through a small aperture A2, moderate amounts of astigmatism will not significantly spoil the image quality. If a patient has a strong astigmatism, correction is desirable. In principle, this correction could be achieved by allowing the patient to wear his/her glasses in the instrument. However, the reflections from such eyeglasses would seriously impair the image quality. An equivalent result which does not create serious reflections is that of mounting the patient's eyeglasses in the optical system in a plane close to the plane of aperture A2 with the same orientation as when worn. A representative mounting 29 for receiving and retaining a lens of a pair of glasses is shown in FIG. 1.

Figure 12:
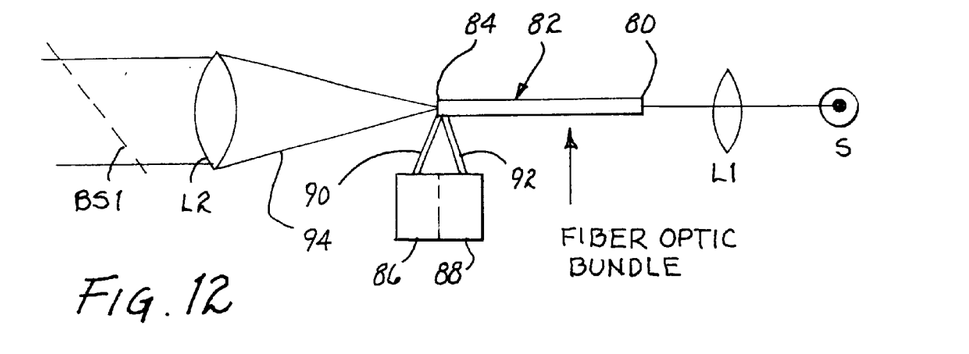
FIG. 12 illustrates a first variant for realigning the optical axis.

In the embodiment of the optical system 8 shown in FIG. 1, the image of aperture A1 is made to move by two axis movement of mirror M1. An alternative apparatus is shown in FIG. 12. One end 80 of an optical fiber or fiber bundle 82 is illuminated by light source S through lens L1. The other end 84 of the fiber bundle serves the same function as aperture A1. Linear actuators, representatively depicted by blocks 86, 88, engage end 84 via elements 90, 92, respectively, to enabled rapid movement of end 84 in the vertical and horizontal directions to realign light path 94 emanating therefrom and passing through lens L2 to beam splitter BS1. Alternatively, if the amount of light from source S may be small, an infrared LED may provide sufficient illumination for all operations, including imaging. In such event, source S and fiber bundle 82 shown in FIG. 13 may be eliminated by mounting the infrared LED in the position occupied by end 84 of the fiber bundle. This configuration is illustrated in FIG. 12 and includes actuators 86, 88 with their respective elements 90, 92 for repositioning the LED vertically and horizontally, as may be required to align the optical axis.

Figure 13:
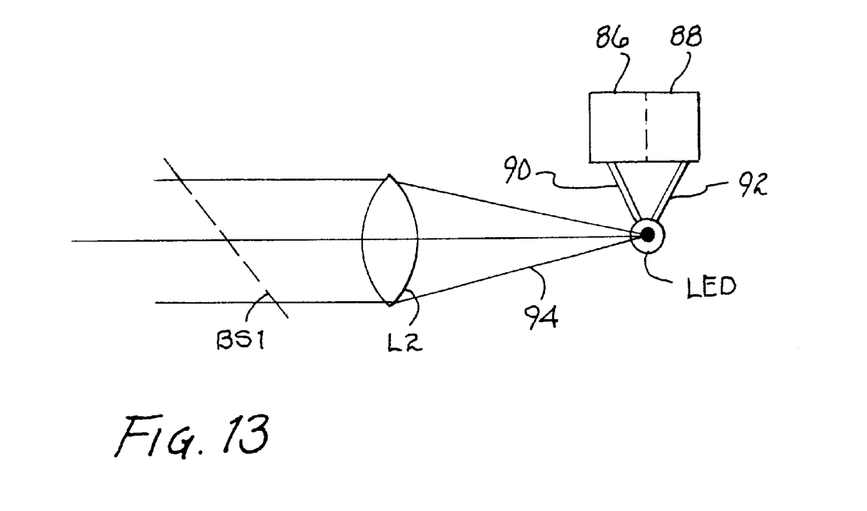
FIG. 13 illustrates a second variant for realigning the optical axis.
Figure 14:
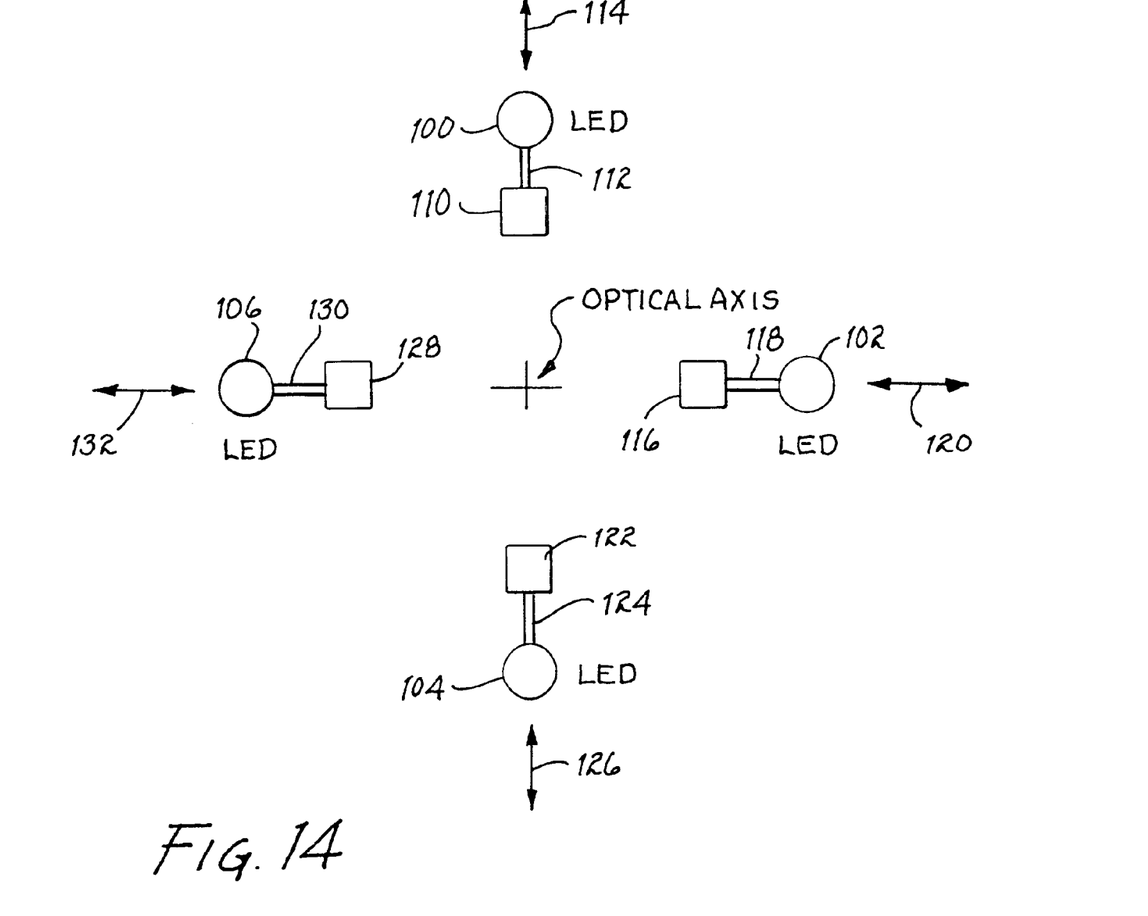
FIG. 14 illustrates a third variant for realigning the optical axis.

Another method/apparatus for providing a small illuminating spot that can be moved with respect to the pupil is to substitute for the LED shown in FIG. 14 a set of four LED's 100, 102, 104 and 106, as shown in FIG. 13. LED 100 is attached to an actuator 110 via an element 112 to reposition the LED vertically, as represented by arrow 114. Actuator 116 is connected to LED 102 via element 118 to bring about horizontal movement, as depicted by arrow 120. Actuator 122 is connected to LED 104 via element 124 to bring about vertical movement of the LED, as depicted by arrow 126. Actuator 128 is connected to LED 106 via actuator 130 to bring about horizontal movement, as depicted by arrow 132. In operation, a selected one of LED's 100, 102, 104 and 106 is illuminated and repositioned so that its image along the optical path falls just inside the edge of the pupil.

While the invention has been described with reference to several particular embodiments thereof, those skilled in the art will be able to make the various modifications to the described embodiments of the invention without departing from the true spirit and scope of the invention. It is intended that all combinations of elements and steps which preform substantially the same function in substantially the same way to achieve the same result are within the scope of the invention.

I claim:

1. Apparatus for imaging the ocular fundus, said apparatus comprising in combination:
   a) a source of illumination for illuminating at least a section of the ocular fundus of a patient;
   b) means for directing the illumination along an optical axis to enter the pupil of the patient;
   c) a video sensor responsive to an image reflected from the eye of the patient for depicting the alignment of the optical axis with the pupil of the patient;
   d) positioning means for aligning the optical axis in response to the depicted alignment;
   e) a focusing assembly for focusing the image of the ocular fundus as a function of the image itself; and
   f) a further video sensor for recording the focused image.

2. The apparatus as set forth in claim 1 including a plurality of photodetectors for detecting light reflection from the iris of the patient and adapted to provide a positioning signal to said positioning means.

3. The apparatus as set forth in claim 1 including at least one fixed point of light upon which the patient fixates to align a section of the ocular fundus of interest with the optical axis.

4. The apparatus as set forth in claim 3 including a plurality of said fixed points of light located at separate locations to expose different sections of the ocular fundus as the patient fixates in turn upon two or more said point of light.

5. The apparatus as set forth in claim 3 including a lens for collimating the illuminating ray along the optical path entering the pupil and a beam splitter disposed in the collimated optical path for reflecting light from each of said fixed points of light to the pupil of the patient.

6. The apparatus as set forth in claim 1 including a mirror disposed in the path of illumination from said source of illumination to the patient's eye and means for relocating said mirror in each of two orthogonal axis to adjust the alignment of the optical axis.

7. The apparatus as set forth in claim 1 including a beam splitter and a lens for directing the reflected image of the ocular fundus toward said video sensor and for creating a reflected image, respectively.

8. The apparatus as set forth in claim 7 including a further beam splitter for reflecting the image to said focusing assembly.

9. The apparatus as set forth in claim 8 wherein said focusing assembly includes said further video sensor.

10. The apparatus as set forth in claim 9 including means for rectilinearly translating said focusing assembly to focus the image of the ocular fundus on said further video sensor.

11. The apparatus as set forth in claim 1 including infrared illuminators for illuminating the eye of the patient to provide an image of the eye at said video sensor.

12. The apparatus as set forth in claim 1 including a computer system for processing the images.

13. The apparatus as set forth in claim 1 wherein said source of illumination has a wavelength in the infrared region.

14. The apparatus as set forth in claim 1 wherein said source of illumination has a wavelength in the near visible infrared region.

15. The apparatus as set forth in claim 1 wherein said source of illumination has a wavelength in the range of visible light.

16. Apparatus for imaging the ocular fundus, said apparatus comprising in combination:
   a) a source of illumination for illuminating at least a section of the ocular fundus of a patient;
   b) means for directing the illumination along an optical axis to enter the pupil of the patient;
   c) a video sensor responsive to an image reflected from the eye of the patient for depicting the alignment of the optical axis with the pupil of the patient;
   d) positioning means for aligning the optical axis in response to the depicted alignment;
   e) a focusing assembly for focusing the image of the ocular fundus as a function of the image itself;

f) a further video sensor for recording the focused image; and g) a head restraint for locating the patient's eye relative to said apparatus, said head restraint comprising at least a part of the frame of a pair of spectacles.

17. The apparatus as set forth in claim 16 wherein the ear pieces of said pair of spectacles are absent.

18. Apparatus for imaging the ocular fundus, said apparatus comprising in combination:

a) a source of illumination for illuminating at least a section of the ocular fundus of a patient;

b) means for directing the illumination along an optical axis to enter the pupil of the patient, said directing means including a fiber optic bundle for receiving illumination at one end from a source and transmitting the received illumination from the other end of said fiber optic bundle along the optical axis;

c) a video sensor responsive to an image reflected from the eye of the patient for depicting the alignment of the optical axis with the pupil of the patient;

d) positioning means for aligning the optical axis in response to the depicted alignment;

e) a focusing assembly for focusing the image of the ocular fundus as a function of the image itself; and f) a further video sensor for recording the focused image.

19. The apparatus as set forth in claim 18 wherein said positioning means includes means for horizontally and vertically repositioning said other end of said fiber optic bundle to align the optical axis of the transmitted illumination with the pupil of the patient.

20. Apparatus for imaging the ocular fundus, said apparatus comprising in combination:

a) a source of illumination for illuminating at least a section of the ocular fundus of a patient;

b) means for directing the illumination along an optical axis to enter the pupil of the patient;

c) a video sensor responsive to an image reflected from the eye of the patient for depicting the alignment of the optical axis with the pupil of the patient;

d) a beam splitter and a lens for directing the reflected image of the ocular fundus toward said video sensor and for creating a reflected image, respectively;

e) positioning means for aligning the optical axis in response to the depicted alignment;

f) a focusing assembly for focusing the image of the ocular fundus as a function of the image itself;

g) a further beam splitter for reflecting the image to said focusing assembly;

h) a further video sensor for recording the focused image; and i) the aerial focal plane of said lens being between said further beam splitter and said focusing assembly and wherein said focusing assembly includes: i) a lens located at its focal distance from the aerial focal plane, ii) an aperture located at the back focal plane of said lens, iii) a further lens for providing a further image, and iv) said further video sensor being located at the back focal plane of said further lens for receiving the image of the ocular fundus section under examination.

21. The apparatus as set forth in claim 20 including a mounting for supporting a lens of the patient's glasses intermediate said lens and said aperture.

22. The apparatus as set forth in claim 20 including means for translating said aperture orthogonally to the optical path of the image between two positions to obtain sequentially two images forming, in combination, a stereo image of the ocular fundus.

23. A method for imaging the ocular fundus, said method comprising the steps of:

a) illuminating at least a section of the ocular fundus of a patient with a source of illumination;

b) directing the illumination along an optical axis to enter the pupil of the patient;

c) depicting the alignment of the optical axis with the pupil of the patient on a video sensor responsive to an image of the eye of the patient;

d) aligning the optical axis in response to the depicted alignment;

e) focusing the image reflected from the ocular fundus as a function of the image itself; and f) displaying the focused image.

24. The method as set forth in claim 23 including the steps of providing a positioning signal from a plurality of photodetectors responsive to light impinging thereupon to carry out said aligning step.

25. The method as set forth in claim 23 including the step of establishing a point of light for the patient to fixate upon to expose a section of interest of the ocular fundus during exercise of said step of illuminating.

26. The method as set forth in claim 23 including the step of capturing the focused image on a further video sensor.

27. The method as set forth in claim 23 wherein said step of illuminating includes the step of illuminating with radiation having a wavelength in the infrared region.

28. The method as set forth in claim 23 wherein said step of illuminating includes the step of illuminating with radiation having a wavelength in the near visible infrared region.

29. The method as set forth in claim 23 wherein said step of illuminating includes the step of illuminating with radiation having a wavelength in the visible light region.

30. A method for imaging the ocular fundus, said method comprising the steps of:

a) restraining movement of a patient's head;

b) initially positioning the patient's eye by exercising a step of locating the patient's head in at least a part of the frame of a pair of spectacles;

c) illuminating at least a section of the ocular fundus of the patient with a source of illumination;

d) directing the illumination along an optical axis to enter the pupil of the patient;

e) depicting the alignment of the optical axis with the pupil of the patient on a video sensor responsive to an image of the eye of the patient;

f) aligning the optical axis in response to the depicted alignment;

g) focusing the image reflected from the ocular fundus as a function of the image itself; and h) displaying the focused image.

31. Apparatus for imaging the ocular fundus, said apparatus comprising in combination:

a) a source of illumination for illuminating at least a section of the ocular fundus of a patient;

b) a first lens for directing the illumination through a first aperture;

c) a filter for controlling the bandwidth of the illumination emanating from said first aperture;

d) a mirror for finely aligning the optical axis of the illumination, said mirror including means for repositioning said mirror in two axes;

e) a first lens for collecting the illumination reflected from said mirror;

f) a second lens for receiving the receiving the collected illumination and forming an image of said aperture in the pupil of the patient to illuminate a section of the ocular fundus of interest;

g) a first beam splitter for receiving the image of the section of the ocular fundus of interest and reflecting the image to a second collecting lens;

h) a third lens for focusing the image received from said first beam splitter upon a first video sensor;

i) a second beam splitter for reflecting a part of the collected light to a fourth lens;

j) a second aperture for passing the image from said forth lens to a third lens;

k) a second video sensor for receiving the collimated image from said third lens; and l) means for relocating said apparatus in three axis to grossly align the optical axis of the ocular fundus illumination with the pupil of the patient.

32. The apparatus as set forth in claim 31 including a source of light and a third beam splitter disposed in the path of the collimated illumination from said first collimating lens to permit the patient to fixate upon said source of light resulting in exposure of the section of the ocular fundus of interest to the illumination.

33. The apparatus as set forth in claim 32 including a plurality of said sources of light at spaced apart locations to correspond with different sections of the fundus being exposed to the illumination.

34. The apparatus as set forth in claim 31 including a plurality of photodetectors for providing a signal responsive to iris reflection.

35. The apparatus as set forth in claim 31 including a further source of light for illuminating the eye of the patient.

36. The apparatus as set forth in claim 31 including a focusing assembly translatable as a unit for focusing the image upon said second video sensor, said focusing assembly comprising said fourth lens, said second aperture, said third collimating lens and said second video sensor and means for rectilinearly translating said focusing assembly.

37. The apparatus as set forth in claim 31 including a mounting for supporting a lens of the patient's pair of glasses adjacent said second aperture.

38. The apparatus as set forth in claim 31 including means for translating said second aperture orthogonally to the axis of the image passing therethrough between a first and a second position to obtain a pair of stereo images having a stereo base equivalent to the distance between said first and second positions.

39. The apparatus as set forth in claim 31 wherein said source of illumination provides illumination having a wavelength in the infrared region.

40. The apparatus as set forth in claim 31 wherein said source of illumination provides illumination having a wavelength in the near visible infrared region.

41. The apparatus as set forth in claim 31 wherein said source of illumination provides illumination having a wavelength in the visible light region.

* * * * *